US008689601B2

(12) United States Patent
Allam

(10) Patent No.: US 8,689,601 B2
(45) Date of Patent: Apr. 8, 2014

(54) OIL DEBRIS MONITOR VERIFICATION DRY RIG

(75) Inventor: Mahdy A. Allam, Glastonbury, CT (US)

(73) Assignee: United Technologies Corporation, Hartford, CT (US)

( * ) Notice: Subject to any disclaimer, the term of this patent is extended or adjusted under 35 U.S.C. 154(b) by 384 days.

(21) Appl. No.: 13/173,118

(22) Filed: Jun. 30, 2011

(65) Prior Publication Data

US 2013/0000376 A1 Jan. 3, 2013

(51) Int. Cl.
*G01N 33/00* (2006.01)
(52) U.S. Cl.
USPC .......................................................... 73/1.03
(58) Field of Classification Search
USPC ............ 73/1.01–1.03, 114.55, 114.56, 865.9; 702/32–36, 65, 72, 152, 175, 183, 189
See application file for complete search history.

(56) References Cited

U.S. PATENT DOCUMENTS

| 3,475,965 | A | 11/1969 | Koblin et al. |
| 4,219,805 | A | 8/1980 | Magee et al. |
| 4,726,434 | A * | 2/1988 | Mosher ....................... 177/25.18 |
| 4,831,362 | A | 5/1989 | Tsaprazis |
| 5,149,962 | A | 9/1992 | Maurice |
| 5,214,377 | A | 5/1993 | Maurice et al. |
| 6,779,414 | B2 | 8/2004 | Shori et al. |
| 6,802,172 | B1 | 10/2004 | Rouse et al. |
| 2002/0007659 | A1 * | 1/2002 | Bennett et al. ................. 73/1.01 |
| 2003/0105600 | A1 * | 6/2003 | Alvi ................................. 702/57 |
| 2004/0140798 | A1 * | 7/2004 | Manneschi ................... 324/239 |

FOREIGN PATENT DOCUMENTS

| EP | 2014877 A2 | 1/2009 |
| GB | 2358252 A | 7/2001 |
| GB | 2425599 A | 11/2006 |

OTHER PUBLICATIONS

Extended European Search Report in counterpart application No. 12166210.0, dated Oct. 5, 2012.

* cited by examiner

*Primary Examiner* — Hezron E Williams
*Assistant Examiner* — Nathaniel Kolb
(74) *Attorney, Agent, or Firm* — Kinney & Lange, P.A.

(57) ABSTRACT

An assembly includes a debris monitor mount, a motor, and a particle belt. The particle belt carries one or more metallic particles. The particle belt is driven by the motor. The particle belt extends proximate the debris monitor mount when driven by the motor.

20 Claims, 3 Drawing Sheets

OIL DEBRIS MONITOR VERIFICATION DRY RIG

STATEMENT OF GOVERNMENT INTEREST

The U.S. Government has a paid-up license in this invention and the right in limited circumstances to require the patent owner to license others on reasonable terms as provided for by the terms of Contract No. N00019-02-C-3003 awarded by Naval Air System Command.

BACKGROUND

The present invention relates to oil debris monitors, and more particularly, to verification of accuracy of oil debris monitors.

Many types of mechanical machinery include various components that require lubrication. For example, gas turbine engines typically have gears and bearings that require a lubricating liquid, such as oil, to lubricate and cool those gears and bearings during operation. During operation, debris accumulates in the lubricating liquid. Because of this, lubrication systems typically include an oil debris monitor system to sense metal debris in the oil. An oil debris monitor system is normally used to flag the initiation or progression of mechanical failures in the lubricated mechanical machinery.

It is extremely difficult to validate the accuracy of an oil debris monitor system while it is installed in a lubrication system. Thus, it is important to validate the accuracy of an oil debris monitor prior to it being installed in the lubrication system. It can also be difficult to reliably validate accuracy of an oil debris monitor in a lab with known validation methods, especially in a lab that does not allow oil to be present.

SUMMARY

According to the present invention, an assembly includes a debris monitor mount, a motor, and a particle belt. The particle belt carries one or more metallic particles. The particle belt is driven by the motor. The particle belt extends proximate the debris monitor mount when driven by the motor.

Another embodiment of the present invention is a method for testing an oil debris monitor. The method includes positioning a belt containing particles detectable by the oil debris monitor in an oil flow passage of the oil debris monitor, moving the belt through the oil flow passage so as to pass the particles through the oil flow passage, and operating the oil debris monitor to test whether the oil debris monitor can detect the particles on the belt.

DETAILED DESCRIPTION

Figure 1:
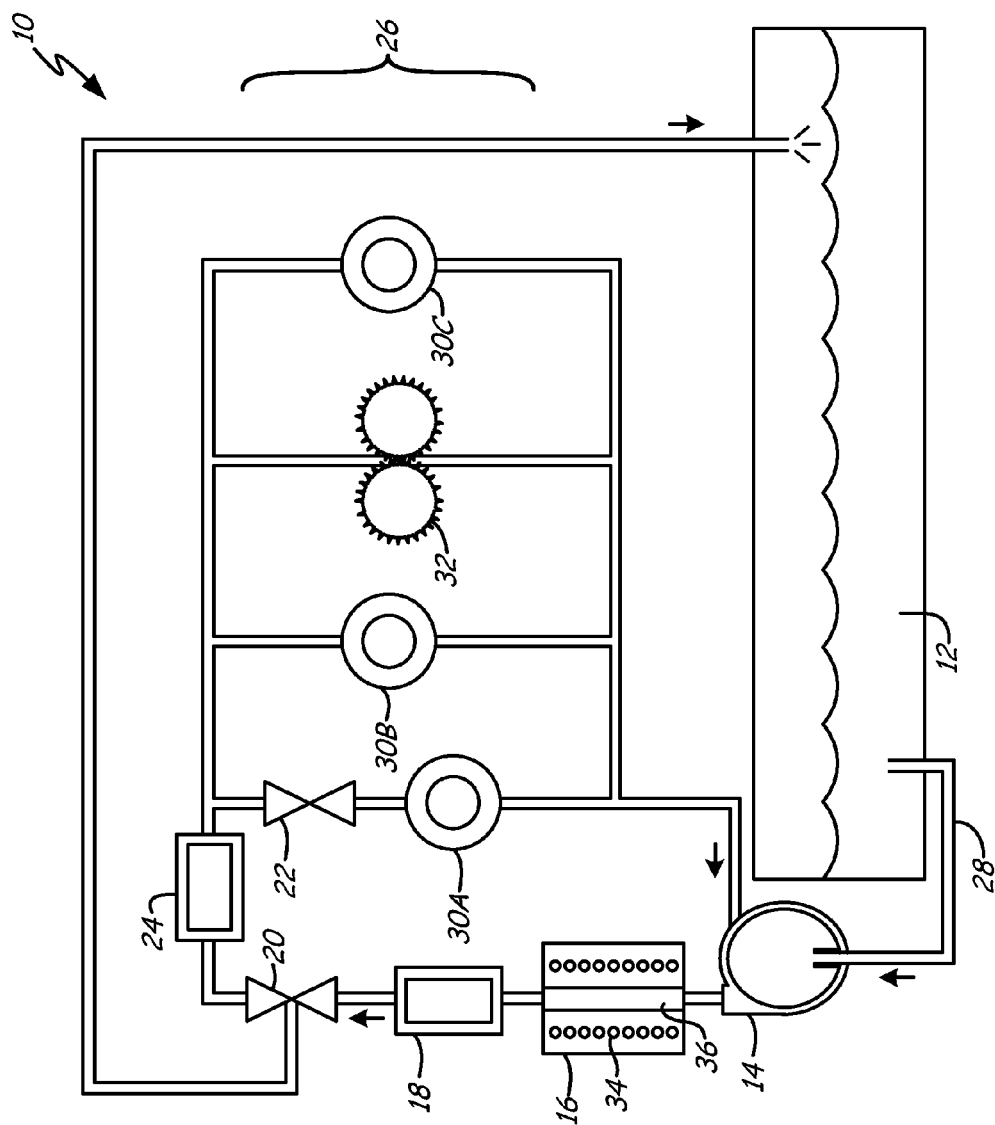
FIG. 1 is a schematic view of a lubrication system including an oil debris monitor.

FIG. 1 is a schematic view of lubrication system 10, which includes oil tank 12, pump 14, oil debris monitor 16, filter 18, valves 20 and 22, cooler 24, and components 26, all fluidically connected by flow passages 28. In the illustrated embodiment, components 26 include bearings 30A-30C and gear train 32.

Pump 14 pumps a lubricating liquid, such as oil through oil debris monitor 16, filter 18, and valves 20 and 22 to components 26. The oil cools components 26, lubricates components 26, and carries debris from lubricated components 26 as it is returned to pump 14. Oil tank 12 is connected between valve 20 and pump 14. Oil tank 12 is used to store extra oil during times that it is not needed by lubrication system 10 for load requirements and to compensate for consumed oil. In one embodiment, lubrication system 10 can be a gas turbine engine lubrication system for lubricating gears and bearings on a gas turbine engine. In other embodiments, oil debris monitor 16 can be used in other lubrication systems that benefit from an accurate oil debris monitor, such as a Diesel engine or other machinery. Oil debris monitor 16 includes one or more coils 34, and also includes flow passage 36 extending through coils 34. Coils 34 detect ferrous and non-ferrous metallic particles passing through flow passage 36. Particle debris detected by oil debris monitor 16 can be indicative of mechanical failure of components 26.

Figure 2:
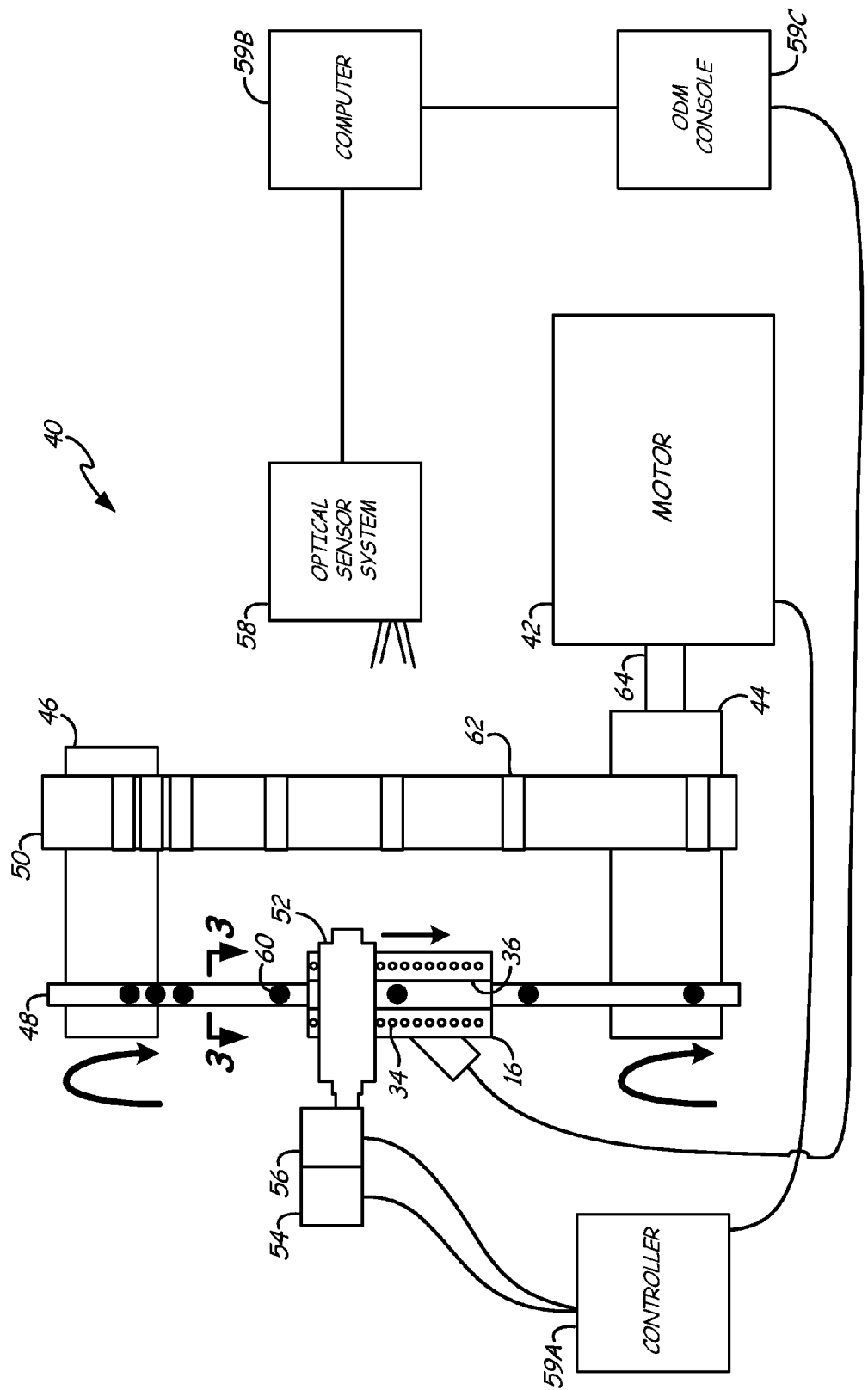
FIG. 2 is a schematic view of a verification rig for verifying the oil debris monitor of FIG. 1.

FIG. 2 is a schematic view of verification rig 40 for verifying oil debris monitor 16. Verification rig 40 includes motor 42, wheels 44 and 46, belts 48 and 50, mount 52, vibrator 54, heater 56, optical sensor system 58, and circuitry 59 (which includes controller 59A, computer 59B, and oil debris monitor console 59C). Mount 52 is a fixture for holding oil debris monitor 16. Belt 48 is a particle belt for carrying metallic particles 60. Particles 60 can be separately spaced along belt 48 or clustered together. In the illustrated embodiment, some particles 60 are spaced apart while other particles 60 are clustered together. Belt 48 extends from wheel 44 to wheel 46, passing proximate mount 52 and through flow passage 36 of oil debris monitor 16. Belt 50 is a particle flagging belt having optical marks 62, each substantially aligned with one of particles 60. Belt 50 also extends from wheel 44 to wheel 46. In the illustrated embodiment, belt 50 has a larger width than that of belt 48. Motor 42 is a variable speed motor, connected to wheel 44 via shaft 64. Wheel 44 has an axis of rotation substantially parallel to that of wheel 46. Belt 50 can be a drive belt, causing wheel 46 to rotate in response to motor 42 rotating wheel 44. This causes belt 48 to move particles 60 through oil debris monitor 16 at a speed proportional to the variable speed of motor 42. This allows a user to control the speed with which particles 60 pass through oil debris monitor 16 during verification. This allows for verification of oil debris monitor 16 at various distinct simulated flow rates.

Controller 59A is connected to and controls motor 42, vibrator 54, and heater 56. Computer 59B is connected to and receives data from optical sensor system 58 and oil debris monitor console 59C. Oil debris monitor console 59C is connected to oil debris monitor 16, and performs data acquisition and signal processing on data received from oil debris monitor 16. The resulting data is then sent by oil debris monitor console 59C to computer 50B. Communication connections can be wired or wireless connections.

Data is collected by computer 59B from both oil debris monitor console 59C and optical system 58 for post processing and comparison. Optical sensor system 58 is positioned with respect to belt 50 so as to sense optical marks 62 on belt 50. Optical sensor system 58 sends a position signal to computer 59B so that computer 59B can record when one or more particles 60 pass through oil debris monitor 16, and consequently determine whether computer 59B receives a correct debris signal from oil debris monitor console 59C. Each optical mark 62 can include a code for various information relating to its corresponding particle 60, such as position, size, and type (e.g. ferrous or other material) of particle 60. This allows optical sensor system 58 to send particle information relating to particles 60 in addition to particle position. Use of optical sensor system 58 allows for more automated verification, thus increasing the reliability of verification performed using verification rig 40.

Alternatively, a user can analyze data on computer 59B without use of optical sensor system 58. For example, by knowing the speed of motor 42 and spacing of particles 60 on belt 48, one can analyze data received from oil debris monitor console 59C to determine whether oil debris monitor 16 is properly detecting particles 60.

Vibrator 54 is connected to mount 52 for vibrating oil debris monitor 16, which is also mounted to mount 52 during verification. This simulates engine vibration, allowing for more accurate simulated engine conditions when verifying oil debris monitor 16. Heater 56 is connected to mount 52 for heating oil debris monitor 16 during verification. This simulates elevated oil temperature, also allowing for more accurate simulated engine conditions when verifying oil debris monitor 16. In alternative embodiments, heater 56 need not be directly mounted to mount 52 so long as heater 56 is positioned proximate mount 52 so as to allow heater 56 to heat oil debris monitor 16. Heater 56 can be virtually any suitable heater, such as a coil wrapped around oil debris monitor 16 or a heating chamber within which oil debris monitor 16 is placed.

Verification rig 40 can be operated by first mounting oil debris monitor 16 to mount 52 and positioning belt 48 in oil flow passage 36. Next, motor 42 rotates wheel 44, which causes belt 50 to rotate wheel 46, and moves belt 48 through flow passage 36 so as to pass particles 60 through flow passage 36. Belt 50 moves at a rate corresponding to that of belt 48. Oil debris monitor 16 can then be operated to verify the ability of oil debris monitor 16 to detect particles 60. While operating oil debris monitor 16, vibrator 54 can vibrate oil debris monitor 16 and heater 56 can heat oil debris monitor 16 so as to more accurately simulate conditions of operation, such as those of a gas turbine engine. Speed of motor 42 can be varied so as to vary the speed of particles 60 passing through oil debris monitor 16. The speed of motor 42 can simulate a minimum expected flow speed and a maximum expected flow speed, and speeds in-between. Vibrator 54 and heater 56 can create vibration and heat conditions that correspond to the simulated flow speeds to ensure oil debris monitor 16 can detect particles during all relevant flow speeds and their associated operating conditions. Together, motor 42, vibrator 54, and heather 56 can simulate various engine running conditions such as engine start, ground idle, snap acceleration, ramp acceleration, and others. While sensing with oil debris monitor 16, optical sensor system 58 detects optical marks 62 that correspond with positioning of particles 60. Oil debris monitor 16 can send debris signals to computer 59B via oil debris monitor console 59C, and optical sensor system 58 can send position signals and/or other particle information to computer 59B. Based upon the debris signals and the particle information signals, computer 59B can be used to compare both data and then determine whether oil debris monitor 16 is operating correctly.

Figure 3:
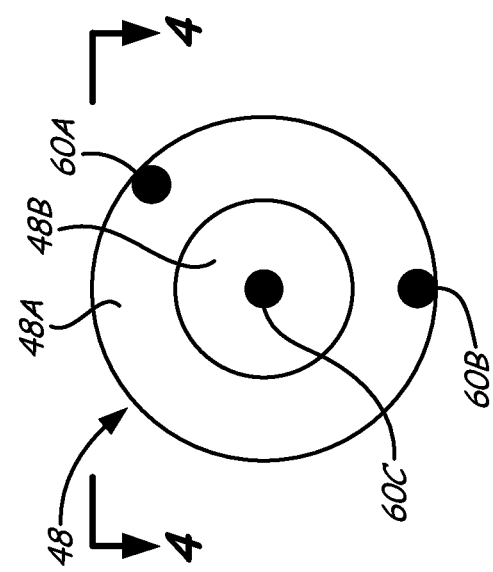
FIG. 3 is a sectional view of a belt of the verification rig taken along line 3-3 of FIG. 2.

FIG. 3 is a sectional view of belt 48 taken along line 3-3 of FIG. 2. Belt 48 has a substantially circular cross section, which includes laminated layers illustrated as radially outer portion 48A and radially inner portion 48B. Radially outer portion 48A and radially inner portion 48B can each be made of one or more flexible non-metallic materials. Particles 60A and 60B are positioned on or in radially outer portion 48A of belt 48. Particle 60C is positioned in radially inner portion 48B of belt 48. Thus, particle 60C is positioned substantially near centerline axis $C_L$ (shown in FIG. 4) and particles 60A and 60B are positioned substantially radially outward of centerline axis $C_L$. In an alternative embodiment, belt 48 can be made of a single non-layered flexible material. In that case, particles 60 can be positioned on and in the single flexible material.

Figure 4:
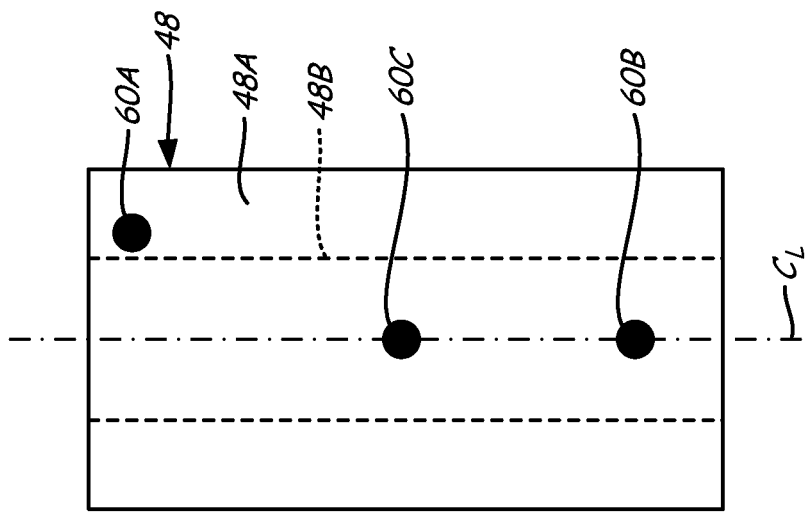
FIG. 4 is the belt of FIG. 3 viewed from the top along line 4-4 of FIG. 3.

FIG. 4 is belt 48 viewed from the top along line 4-4 of FIG. 3. Particles 60A, 60B, and 60C are spaced apart from one another along a length of belt 48. This allows for each particle 60 to be sensed independently by oil debris monitor 16 (shown in FIGS. 1 and 2) for verification. Though particles 60B and 60C both appear to be aligned with centerline axis $C_L$ as viewed from this angle, particle 60B is actually positioned on or in radially outer portion 48A (as shown in FIG. 3). Together, FIGS. 3 and 4 show that particles 60 can be positioned in and on belt 48 at various radial, axial, and circumferential positions. Such positioning allows one to verify the ability of oil debris monitor 16 to detect particles at various positions in a simulated flow stream.

The features of verification rig 40 have numerous benefits and advantages. First, verification rig 40 is a "dry" rig, in that it does not require the use of oil to validate oil debris monitor 16. This allows verification rig 40 to be operated in a clean laboratory that does not allow the presence of oil, such as an Electronic Verification Bench. Second, verification rig 40 allows for more accurate simulation of operating conditions such as heat, vibration, and flow speed. Third, verification rig 40 allows for particles 60 to be positioned and spaced as desired for testing. This all allows a user to more accurately test and verify accuracy of an oil debris monitor's ability to detect debris particles.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims. Thus, verification rig 40 need not be precisely as illustrated so long as it includes the features as claimed below. For example, optical marks 62 need not be positioned on belt 50 so long as optical marks 62 can be sensed by optical sensor system 58 and correspond to one or more particles 60. Moreover, optical sensor system 58 could be omitted and replaced with another suitable system for flagging position and/or other information relating to particles 60.

The invention claimed is:

1. An assembly comprising:
    a debris monitor mount;
    a motor; and
    a particle belt carrying one or more metallic particles, wherein the particle belt is driven by the motor, and wherein the particle belt extends proximate the debris monitor mount and through an oil flow passage when driven by the motor.

2. The assembly of claim 1, and further comprising:
    an oil debris monitor mounted to the debris monitor mount.

3. The assembly of claim 1, wherein the belt comprises only non-metallic material except for the metallic particles.

4. The assembly of claim 1, and further comprising:
    a driving wheel driven by the motor; and a second wheel having an axis of rotation substantially parallel to that of the driving wheel, wherein the particle belt extends from the driving wheel to the second wheel.

5. The assembly of claim 4, and further comprising:
a second belt extending from the driving wheel to the second wheel, wherein the second belt is larger than the particle belt, and wherein the second belt drives rotation of the second wheel when the driving wheel rotates.

6. The assembly of claim 4, and further comprising:
a second belt extending from the driving wheel to the second wheel; and
an optical sensor positioned with respect to the second belt so as to sense optical marks on the second belt.

7. The assembly of claim 1, wherein the particle belt has a substantially circular cross section.

8. The assembly of claim 7, wherein the metallic particles include a first particle positioned substantially near a centerline axis of the particle belt and a second particle positioned substantially radially outward from the centerline axis.

9. An oil debris monitor test assembly comprising:
a mount;
an oil debris monitor attached to the mount, wherein the oil debris monitor includes an oil flow passage;
a motor; and
a belt driven by the motor, wherein the belt extends through the oil flow passage, and wherein the belt contains particles detectable by the oil debris monitor.

10. The assembly of claim 9, and further comprising:
a vibrator connected to the mount.

11. The assembly of claim 9, and further comprising:
a heater positioned proximate the oil debris monitor for heating the oil debris monitor.

12. The assembly of claim 9, wherein the oil debris monitor comprises at least one coil, and wherein the belt passes through the coil.

13. The assembly of claim 9, wherein the particle belt has a substantially circular cross section, and wherein the particles include a first metallic particle positioned substantially near a centerline axis of the particle belt and a second metallic particle positioned substantially radially outward from the centerline axis.

14. A method for testing an oil debris monitor, the method comprising:
positioning a belt containing particles detectable by the oil debris monitor in an oil flow passage of the oil debris monitor;
moving the belt through the oil flow passage so as to pass the particles through the oil flow passage; and
operating the oil debris monitor to test whether the oil debris monitor can detect the particles on the belt.

15. The method of claim 14, and further comprising:
vibrating the oil debris monitor while operating the oil debris monitor.

16. The method of claim 14, and further comprising:
heating the oil debris monitor with a heater while operating the oil debris monitor.

17. The method of claim 14, and further comprising:
driving a variable speed motor to move the belt; and
varying speed of the variable speed motor while operating the oil debris monitor.

18. The method of claim 14, and further comprising:
detecting optical marks that correspond with positioning of the particles on the belt using an optical sensor; and
determining whether the oil debris monitor is operating correctly based upon data from the optical sensor and the oil debris monitor.

19. The method of claim 18, wherein the optical marks include a first optical mark aligned with a first metallic particle and a second optical mark aligned with a second metallic particle.

20. The method of claim 19, wherein the belt is a first belt, wherein the first and second optical marks are positioned on a second belt, wherein the second belt is moved at a rate corresponding to that of the first belt.

* * * * *